US00PP29146P2

(12) United States Plant Patent
Dodd et al.

(10) Patent No.: US PP29,146 P2
(45) Date of Patent: Mar. 27, 2018

(54) APPLE TREE NAMED 'MAIA11'

(50) Latin Name: *Malus×domestica*
Varietal Denomination: MAIA11

(71) Applicants: William Dodd, Newcomerstown, OH (US); David Doud, Wabash, IN (US); John Mitchell Lynd, Pataskala, OH (US); Gregory Miller, Carrollton, OH (US)

(72) Inventors: William Dodd, Newcomerstown, OH (US); David Doud, Wabash, IN (US); John Mitchell Lynd, Pataskala, OH (US); Gregory Miller, Carrollton, OH (US)

( * ) Notice: Subject to any disclaimer, the term of this patent is extended or adjusted under 35 U.S.C. 154(b) by 0 days.

(21) Appl. No.: 15/330,373

(22) Filed: Sep. 12, 2016

(51) Int. Cl.
*A01H 5/08* (2006.01)

(52) U.S. Cl.
USPC ..... Plt./161

(58) Field of Classification Search
USPC ..... Plt./161
CPC ..... A01H 5/0875
See application file for complete search history.

*Primary Examiner* — Kent L Bell

(57) ABSTRACT

A new and distinct variety of apple tree was identified from a population of seedlings derived from a cross of 'Honeycrisp' and 'Fuji'. The new variety, named 'MAIA11', is distinct from 'Honeycrisp' as 'MAIA11' ripens early-October, 3 weeks after 'Honeycrisp' . 'MAIA11' is distinct from 'Fuji' as 'MAIA11' ripens 3 weeks before 'Fuji'. 'MAIA11' fruit are medium sized, extremely crisp, with simple sweet-tart flavor and long storability.

2 Drawing Sheets

Latin name of the genus and species of the plant claimed: *Malus×domestica.*

Variety denomination: 'MAIA11'.

BACKGROUND OF THE INVENTION

A new and distinct variety of apple tree was identified from a population of seedlings derived from a cross of 'Honeycrisp' (U.S. Plant Pat. No. 7,197) and 'Fuji' (not patented—original strain originating from a cross of 'Delicious' (not patented) and 'Ralls Janet' (not patented) made in Japan and released as a variety in 1962). This cross was made as a part of the Midwest Apple Improvement Association apple breeding project. This superior seedling tree was identified in a population of seedlings from this cross at Wabash, Ind.

The seedling tree was planted as a 1-year-old tree at Wabash, Ind. in 2001 and grown among a population of several hundred siblings. Evaluations of fruit quality and tree growth parameters were begun in 2005 and this seedling was identified over several years as superior based upon tree growth habit, precocity, superior fruit quality, and harvest time. Utilizing grafting reproduction, the new apple tree variety was asexually propagated by David Doud in 2010 at Wabash, Ind. and has been observed to remain true to the description set forth herein.

The new variety, named 'MAIA11', is distinct from 'Honeycrisp' as 'MAIA11' ripens early-October, 3 weeks after 'Honeycrisp' (Table 1). 'MAIA11' is distinct from 'Fuji' as 'MAIA11' ripens 3 weeks before 'Fuji'. 'MAIA11' fruit (FIG. 1) are medium sized, extremely crisp, with simple sweet-tart flavor and long storability. The closest comparison variety to 'MAIA11' is, 'MAIA1', claimed in U.S. Plant Pat. No. 24,579. 'MAIA11' has a crispier flesh, has ribbed form instead of oblate regular, and matures 10 days earlier than 'MAIA1'.

BRIEF DESCRIPTION OF THE DRAWINGS

The accompanying photographs show typical specimens of the new variety depicted in color as true as is reasonably possible. 'MAIA11' photographs were taken in Canfield, Ohio.

DETAILED BOTANICAL DESCRIPTION

Figure 1:
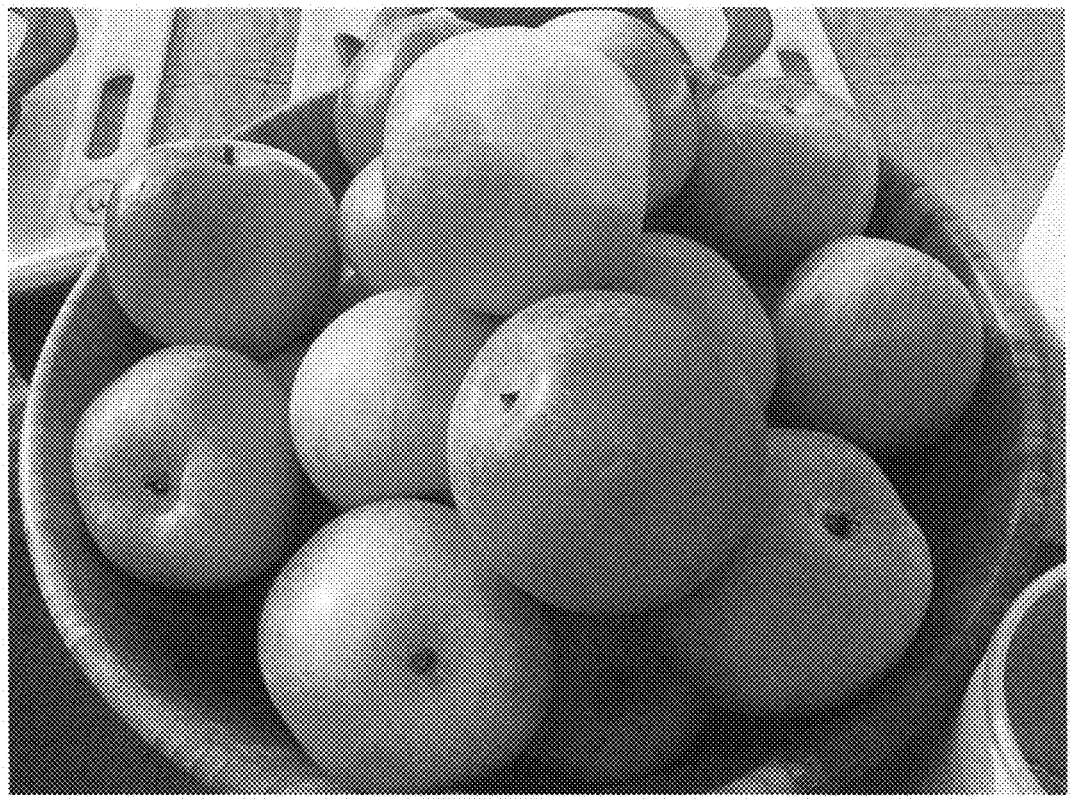
FIG. 1. Typical fruit of 'MAIA11' post-harvest.
Figure 2:
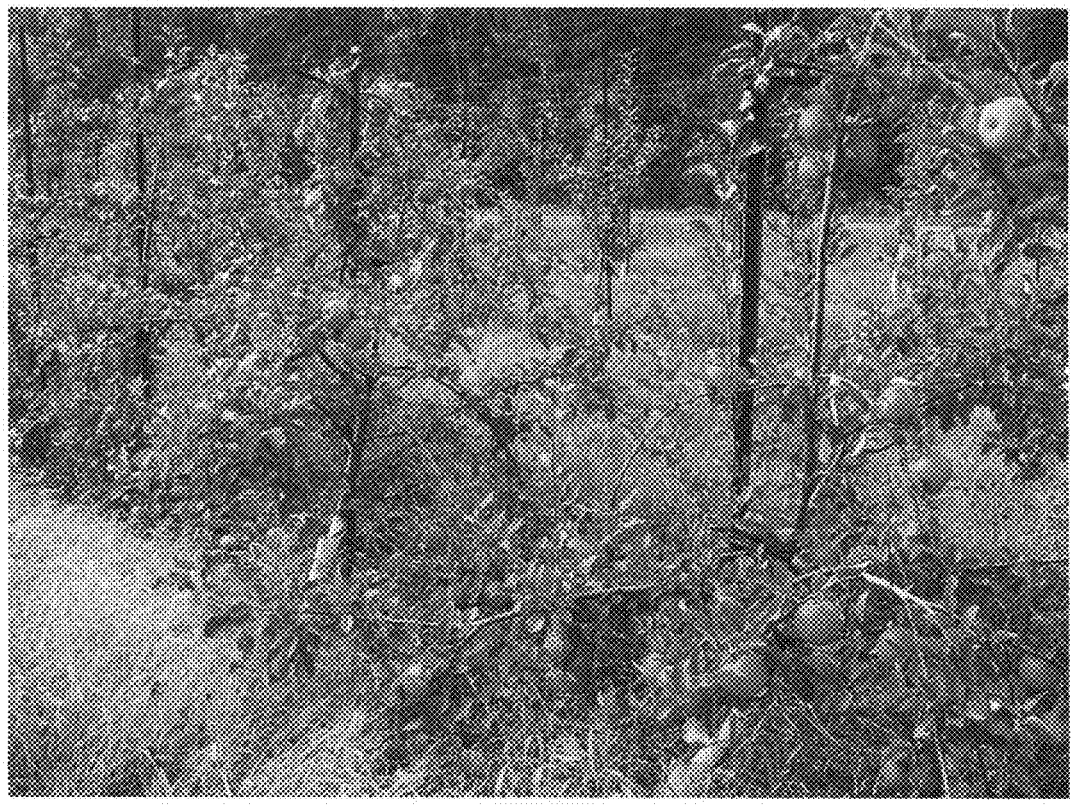
FIG. 2 Typical 'MAIA11' trees bearing fruit in September in Ohio.

Color references are made to The Royal Horticultural Society Color Chart (R.H.S.) 2001 Edition.

Parentage: 'Honeycrisp' female parent and 'Fuji' male parent; controlled cross made by Greg Miller at Pataskala, Ohio in 1999.

Original seedling tree:
- *Age.*—17 years.
- *Size.*—15' height, 15' spread.
- *Vigor.*—Medium.
- *Form.*—Round, spreading.
- *Production.*—Very productive.
- *Growth type.*—Spindle tree growth form, productive spurs located throughout tree.
- *Bearing.*—Annual.

Trunk:
- *Original seedling tree size.*—16 cm at 15 cm height.
- *Bark color.*—Greyed-Green 197B.
- *Lenticels.*—Oblong; 1 mm×5 mm.
- *Lenticel color.*—Grey-Brown N199D.
- *Lenticel density.*—4-6 lenticels/cm$^2$.

Branches:
- 3 *year old.*—9-15 mm in diameter, branch angle 80-90°; Grey-Brown 197B; typical branch length of 25-38 cm.

2 *year old.*—4-7 mm in diameter, branch angle 80-90°; Grey-Brown 199A; typical branch length of 20-30 cm.

1 *year old.*—4-5 mm in diameter, branch angle 80-90°; Grey-Brown 199B; typical branch length of 15-20 cm.

Leaves:

*Size.*—Length 90-106 mm; width 55-96 mm.

*Texture.*—Leathery, crisp.

*Form.*—Ovate.

*Base.*—Roundly cuneate.

*Apex.*—Acute.

*Adaxial surface pubescence.*—None.

*Abaxial pubescence.*—Finely pubescent.

*Adaxial surface color.*—Green Group 137B.

*Abaxial surface color.*—Green Group 138B.

*Veination.*—Pinnate; 10-12 major veins; mainly alternate; Yellow-Green 149D.

*Margin.*—Serrate.

*Petiole length.*—29-43 mm.

*Petiole width.*—2 mm.

*Petiole adaxial color.*—Yellow-Green 144D to Greyed-Purple 185C toward base and abscission layer on larger leaves.

*Petiole adaxial surface color.*—Yellow-Green 144D to Greyed-Purple 185C toward base.

*Petiole groove.*—Very shallow, depth 0.1 mm.

*Stipules.*—Present; 5 mm length; 1 mm width; Yellow-Green 146C.

*Leaf glands.*—None observed.

Leaf buds:

*Shape.*—Both lateral and terminal buds pointed with imbricate scales.

*Length.*—4-5 mm

*Width.*—3 mm

*Color.*—Yellow-Green 145A with Greyed-Purple 187A overtones.

*Placement on branch.*—Alternate, oppressed against wood.

*Internode distance.*—24-30 mm.

Spurs:

*Length.*—Varies from 10-100 mm.

*Proportion.*—10-49 mm=15. 50-100 mm=5. This Proportion means that for every spur that is 50-100 mm in length, there are 3 spurs that are 10-49 mm in length Width: 3-5 mm.

Flowers at popcorn stage:

*Pedicel.*—Length 16-23 mm; diameter 1.5-2 mm.

*Pedicel color.*—Greyed-Green 191C.

*Bud.*—Length 8-11 mm; width 8-12 mm.

*Bud color.*—Red-Purple Group 63B to Red-Purple Group 69C.

Flowers at full bloom:

*Bloom time.*—Depends on spring temperatures, but with 'Golden Delicious'; typically during the fourth week of April in northern Ohio.

*Bloom period.*—Depends on spring temperatures, but first spur blossoms and then lateral blossoms on one-year wood; approximately 7 days.

*Presentation.*—Showy.

*Fragrance.*—Aromatic.

*Fertility.*—Fertile.

*Number of flowers per cluster.*—4-6 with 5 typical.

Petals:

*Arrangement.*—5 petals/flower.

*Color.*—Upper surface (inside) White 155C; lower surface (outside) White 155C with shades of Red-Purple N155B.

*Shape.*—Broadly ovate, abruptly cuneate at junction with receptacle.

*Petal apex description.*—predominantly rounded with some fluting.

*Veins.*—Non-distinct.

*Margins.*—Somewhat ruffled with occasional notching at the apex.

*Texture.*—Soft.

*Receptacle.*—Length 5 mm; width 3-4 mm; color Greyed-Green 191C.

*Pedicel.*—Length 14-23 mm; width 2 mm; color Greyed-Green 191C.

*Sepals.*—5/flower; wedge-shaped; sharply pointed; length 5-7 mm; width 3 mm at widest point; adaxial and abaxial color Greyed-Green 192A with Greyed-Purple 186A at tips.

*Stamens.*—14-18 in number.

*Anthers.*—Length 2-3 mm; width 1.5-2 mm; color Yellow Group 2C.

*Pollen.*—Present and abundant; color; Yellow Group 10B.

*Filaments.*—Length 8 mm; width 0.5-1 mm; color Greyed-Green 157B.

*Pistil.*—Held lower than anthers in majority of blossoms.

*Ovary.*—Length 4 mm; width 4 mm; color Green Group 143C.

*Style.*—Length 8-10 mm from base to stigma; fused base; color Greyed-Green 192C; 5 Styles are fused in bottom 1 mm. color Greyed-Green 195B.

Pollination requirements: Requires cross-pollination from diploid varieties with overlapping bloom; will pollinate diploid varieties of overlapping bloom.

Fruit:

*Maturity when described.*—6 weeks storage.

*Date of picking.*—Oct. 7, 2015.

*Size.*—Axial diameter 66-89 mm; Transverse diameter 30-61 mm.

*Fruit weight.*—158-242 g, average 172.

*Form.*—Ribbed.

*Cavity.*—Acuminate medium deep; russet extending out of cavity.

*Basin.*—Star-shaped, shallow, wide, wavy, symmetrical; width 30 mm.

*Calyx.*—Closed, pointy, tight-converging.

Skin:

*Thickness.*—Medium.

*Tendency to crack.*—Little, cracks more on dry years.

*Lenticels.*—Round shape.

*Lenticel diameter.*—0-1 mm.

*Color.*—Red Group 46B.

*Stripes.*—Light striping; Color: Red Group 46B.

*Ground color.*—Yellow-Green 154D.

Flesh:

*Aroma.*—Sweet, mild.

*Color.*—Yellow-White 158C.

*Texture.*—Firm, crisp, breaking, juicy, sweet.

*Eating quality.*—Excellent.

Core: Small.

*Locule number per fruit.*—5.

*Bundle area.*—1005 $mm^2$.

*Bundle.*—Inconspicuous.

*Carpel axial length.*—9-10 mm.

*Seed cells.*—Walls thin, weak.

Seeds:

*Number perfect.*—9-14.

*Number in one cell.*—0-4.

*Length.*—9 mm.

*Breadth.*—5 mm.

*Color.*—Greyed-Orange 166B; seeds often partially covered with white parenchymous tissue.

Stem:

*Length.*—20-30 mm.

*Width.*—2 mm.

*Color.*—Greyed-Yellow 162B.

Use: Fresh market; dessert; fruit brix 14-19% Yield 2.5 bushel/tree @300 trees/acre=750 bushels/acre annually.

Shipping quality: Good.

Keeping quality: Better than average for domestic apple. 14 weeks in refrigerated storage.

Drought tolerance: Average for domestic apple.

Tree winter hardiness: Average for domestic apple.

Disease:

*Resistance.*—Slight resistance to fireblight (*Erwinia amylovora*).

*Susceptibility.*—Susceptible to apple scab (*Venturia inaequalis*), powdery mildew (*Podosphaera leucotricha*) and other fungal diseases.

TABLE 1

First Harvest Dates for 'MAIA11' in 3 Midwestern Locations

| | 2013 | 2014 | 2015 |
|---|---|---|---|
| Canfield, OH | Sep. 27 | Sep. 25 | Sep. 27 |
| Pataskala, OH | Sep. 25 | Sep. 23 | Sep. 25 |
| Orchard, Wabash, IN | Sep. 27 | Sep. 24 | Sep. 27 |

What is claimed is:

1. A new, distinct variety of apple tree named 'MAIA11', as illustrated and described herein.

* * * * *